(12) United States Patent
Thomas et al.

(10) Patent No.: US 9,187,505 B2
(45) Date of Patent: Nov. 17, 2015

(54) HOMOLEPTIC RARE EARTH TRIARYL COMPLEXES

(75) Inventors: Oliver Thomas, Marburg (DE); Jörg Sundermeyer, Marburg (DE)

(73) Assignee: Rockwood Lithium GmbH, Frankfurt am Main (DE)

( * ) Notice: Subject to any disclaimer, the term of this patent is extended or adjusted under 35 U.S.C. 154(b) by 0 days.

(21) Appl. No.: 14/235,285

(22) PCT Filed: Aug. 2, 2012

(86) PCT No.: PCT/EP2012/003293
§ 371 (c)(1),
(2), (4) Date: Jan. 27, 2014

(87) PCT Pub. No.: WO2013/017281
PCT Pub. Date: Feb. 7, 2013

(65) Prior Publication Data
US 2014/0155562 A1    Jun. 5, 2014

(30) Foreign Application Priority Data
Aug. 2, 2011  (DE) .......................... 10 2011 080 285

(51) Int. Cl.
| | | |
|---|---|---|
| *C07F 9/53* | (2006.01) | |
| *C07F 9/535* | (2006.01) | |
| *C08G 69/00* | (2006.01) | |
| *C08G 69/14* | (2006.01) | |
| *C08G 63/00* | (2006.01) | |
| *C08G 63/84* | (2006.01) | |
| *C08F 4/52* | (2006.01) | |
| *C08F 36/08* | (2006.01) | |
| *C08F 136/08* | (2006.01) | |
| *C08F 4/54* | (2006.01) | |
| *C08G 63/82* | (2006.01) | |

(52) U.S. Cl.
CPC .............. *C07F 9/5345* (2013.01); *C07F 9/5352* (2013.01); *C08F 4/52* (2013.01); *C08F 4/545* (2013.01); *C08F 36/08* (2013.01); *C08F 136/08* (2013.01); *C08G 63/00* (2013.01); *C08G 63/823* (2013.01); *C08G 63/84* (2013.01); *C08G 69/00* (2013.01); *C08G 69/14* (2013.01)

(58) Field of Classification Search
CPC ............ C08F 4/52; C08F 4/545; C08F 10/00; C08F 36/08; C08F 136/08; C08L 77/00; C08L 77/02; C08G 63/00; C08G 63/84; C08G 69/00; C08G 69/14; C07F 9/5345; C07F 9/5352

See application file for complete search history.

(56) References Cited

PUBLICATIONS

Bennett, et al. "Complexes of platinum(II), platinum(IV), rhodium(III) and iridium(III) containing orthometallated triphenylphosphine", J. Chem. Soc., Dalton Trans., (2000), pp. 3537-3545.
Booij, et al. C-H Activation of Arenes and Substituted Arenes by the Yttrium Hybride (Cp*2YH)2:Competition between Cp* Ligand Metalation, Arene Metalation, and H/D Exchange. Molecular Structures of Cp*2Y(μ-H)(μ-η1, η5-CH2C5Me4)YCp* and Cp*2Y(o-C6H4PPh2CH2), Organometallics, 12 (1993), pp. 3531-3540.
Castillo, et al. "Synthesis of Sm—SiH3 complexes via σ-Bond Metathesis of the Si—C Bond of Phenylsilane", Organometallics, 19 (2000), pp. 4733-4739.
Depree, et al. "Cyclomanganagted derivatives of triphenylphosphine chalcogenides", J. of Organometallic Chemistry, 533 (1997), pp. 143-151.
Ramirez, et al. "Communications—A New Tyope of Azo Compound by Coupling at the Cyclopentadienide Ring", ACS Publications, J. Org, Chem., 21(11), (1956), pp. 1333-1333.
Schaub, et al. "New Evidence for and New Reactions of Ortho-Lithio Ylids", Tetrahedron Letters, 26 (13), (1985), pp. 1623-1626.
Schumann, et al. "XX. Cyclopentadienyllutetiumderivate von triphenylmethylenphosphoran", J. of Organometallic Chemistry, 269 (1984), pp. 21-27. [English Abstract Only].
Thomas, Oliver "Homoleptic Tris-Aryl Complexes of the Rare Earth Metals. XX. Tage der Selten Erden—Terrae Rarae 2007", XP055043795.
Thomas, Oliver "Homoleptic Tris-Aryl Complexes of the Rare Earth Metals. XX. Tage der Selten Erden 2008", XP055043798.
Watson, Patricia L. "Facile C-H Activation by Lutetium-Methyl and Lutetium-Hydride Complexes", J. Chem. Soc., Chem.Commun. (1983), pp. 276-277.

*Primary Examiner* — Caixia Lu
(74) *Attorney, Agent, or Firm* — Norton Rose Fulbright US LLP

(57) ABSTRACT

The invention relates to chelate-stabilized homleptic triaryl compounds based on phenylphosphoranes, to methods for preparing same and to the use thereof as catalysts. According to the invention, the object is achieved by homleptic rare earth triaryl complexes of the general formula (I), where SE=Sc, Y, La, Ce, Pr, Nd, Pm, Sm, Eu, Gd, Tb, Dy, Ho, Er, Tm, Yb or Lu; X=O, CRR'; $R^1$, $R^2$=phenyl; R, R'=mutually independently H, alkyl with n=10 C atoms, phenyl or trimethylsilyl.

14 Claims, No Drawings

HOMOLEPTIC RARE EARTH TRIARYL COMPLEXES

This application is a §371 of International Application No. PCT/EP2012/003293 filed Aug. 2, 2012, and claims priority from German Patent Application No. 10 2011 080 285.1 filed Aug. 2, 2011.

The present invention relates to chelate-stabilized homoleptic triaryl compounds based on phenylphosphoranes and to methods for preparing same and to the use thereof as catalysts.

Compounds of the cyclometalated triphenylphosphinoxide ligands (TPPO, according to FIG. 1) are scarce in the literature.

FIG. 1: The TPPO ligand and the cyclometalated variant thereof

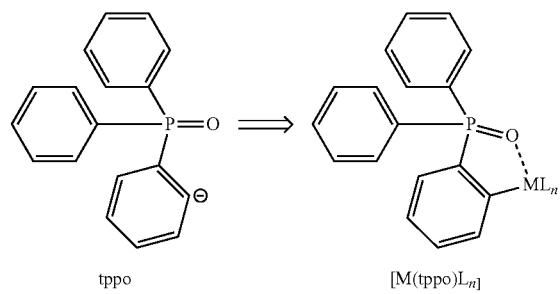

tppo      [M(tppo)L$_n$]

Weichmann et al. published compounds of this ligand in form of a series of Sn(IV) complexes with a Lewis-azide main group element (Abicht, H. P.; Weichmann, H., Z. *Chem.* 1988, 28, (2), 69-70). In addition, it was possible to provide a structural characterization of [Sn(TPPO)Me$_2$Cl] for the first time.

FIG. 2: Sn(IV) compounds of the TPPO ligand[2]

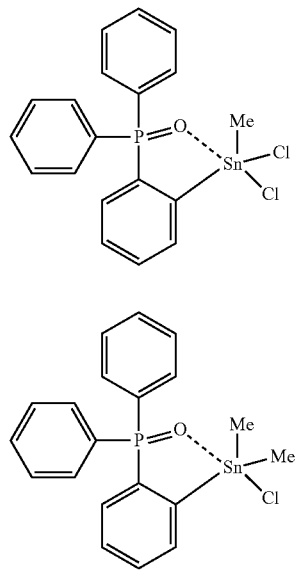

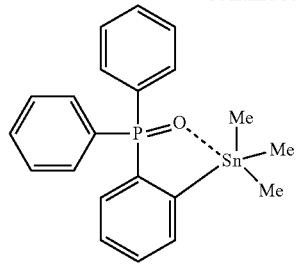

Further compounds of the [M(TPPO)L$_n$] type could be obtained with [MnBz(CO)$_5$], eliminating toluene, and an equivalent CO. The compound [Mn(TPPO)(CO)$_4$] also underwent crystallographical analysis (Depree, G. J.; Childerhouse, N. D.; Nicholson, B. K., *J. Organomet. Chem.* 1997, 533, (1-2), 143-151). The first homoleptic compound was produced by reacting HgCl$_2$ with LiC$_6$H$_4$PPh$_2$ followed by oxidation of the anionic phosphine ligand with aqueous H$_2$O$_2$—the [Hg(TPPO)$_2$] also underwent structural characterization. A further compound of a late transitional metal was synthesized in a similar fashion. The oxidation of [o-Pt(C$_6$H$_4$PPh$_2$)$_2$] with elemental bromine yielded inter alia [Pt(TPPO)$_2$Br$_2$] (Bennett, M. A.; Bhargava, S. K.; Ke, M.; Willis, A. C., *J. Chem. Soc, Dalton Trans.* 2000, 3537-3545).

FIG. 3: TPPO compounds of medium and late transitional metals

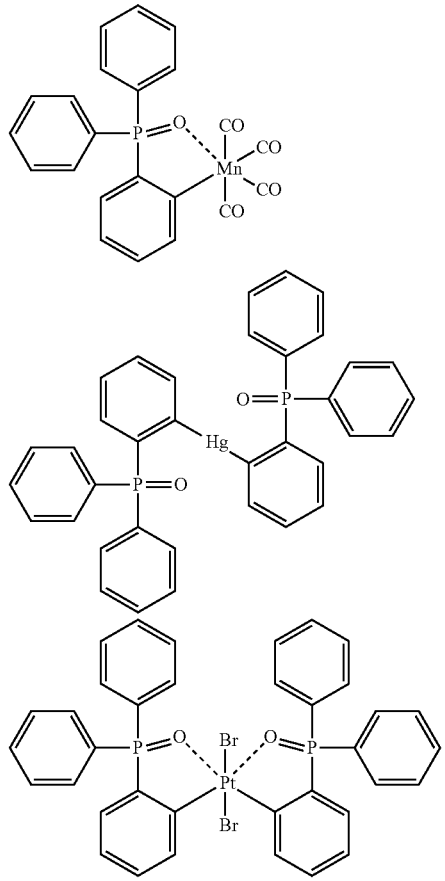

Tilley et al. were first in successfully inserting the TPPO ligand into a rare earth metal. Due to the sterically enormously demanding pentamethylcyclopentadienyl ligands, it was possible to obtain [Cp*$_2$Sm(TPPO)] as a molecularly stable compound. The preparation was achieved either starting from [Cp*$_2$SmSiH$_3$(O=PPh3)] at elevated temperatures or by the elimination of hydrogen from [Cp*$_2$SmO(μ-H)]$_2$ and two equivalents triphenylphosphine oxide. The characterization was done exclusively by NMR spectroscopy (Castillo, I.; Tilley, T. D., *Organometallics* 2000, 19, (23), 4733-4739).

FIG. 4: Synthesis of [Cp*$_2$Sm(TPPO)] via two different paths according to Tilley et al.

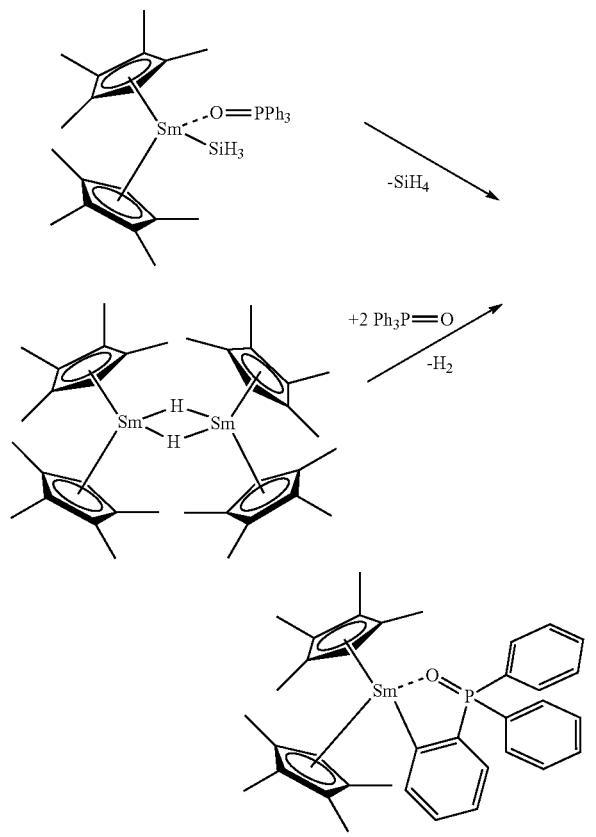

The reaction of phosphorane A with tert-butyllithium in THF-d$_8$ at −78° C. yields only the ortho-metalated product, as could be documented by NMR-spectroscopic analysis.

FIG. 5: Synthesis of the lithiated triphenylmethylidene phosphorane

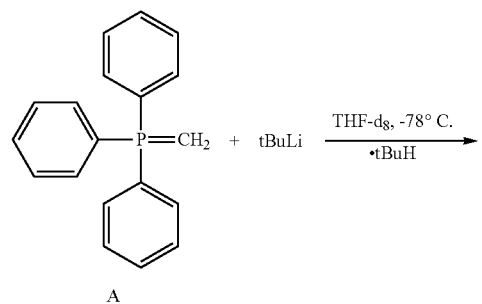

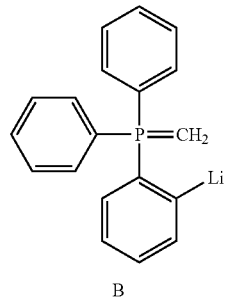

The metalated compounds B only have very minimal thermal stability at temperatures above −15° C., after which point they quickly degrade to compound C, due to the intramolecular addition of the singlet carbene B' to a neighboring phenyl ring and subsequent elimination of benzene (Schaub, B.; Schlosser, M., *Tetrahedron Lett.* 1985, 26, (13), 1623-1626).

FIG. 6: Degradation reaction of lithiated triphenylmethylidene phosphorane

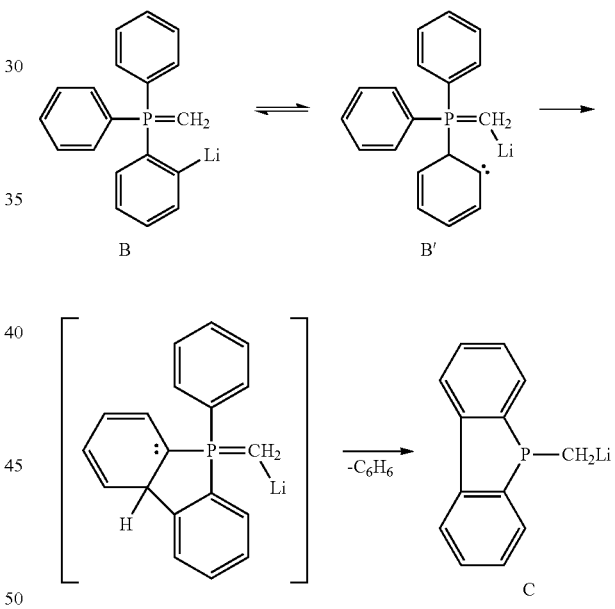

Rare earth metals have only in few cases been combined with the anionic TPPM ligand. Stabilizing these compounds could always be achieved by cyclopentadienyl ligands or the permethylated derivatives thereof. The first representative thereof was published as compound D in 1984 by WATSON (Watson, P. L., *J. Chem. Soc, Chem. Commun.* 1983, (6), 276-277). Shortly thereafter, compound E followed as the result of works by SCHUMANN et al. (Schumann, H.; Reier, F. W., *J. Organomet. Chem.* 1984, 269, (1), 21-27). With complex F in 1993, a compound of this class was obtained for the first time that was also structurally characterized, (Booij, M.; Deelman, B. J.; Duchateau, R.; Postma, D. S.; Meetsma, A.; Teuben, J. H., *Organometallics* 1993, 12, (9), 3531-3540).

FIG. 7: Known rare earth compounds with the TPPM ligand

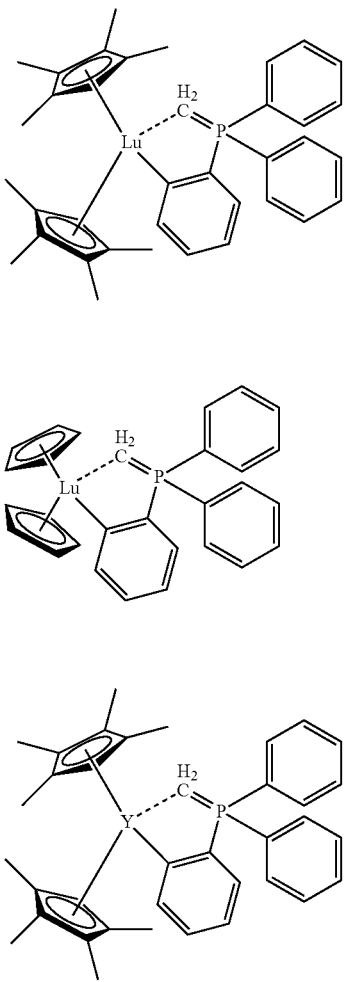

Therefore, it is the object of the present invention to describe novel homoleptic rare earth triaryl complexes, processes for preparing such complex compounds and for testing the properties thereof.

This object is achieved according to the invention by homoleptic rare earth triaryl complexes (Rare Earth=RE) of the general formula 1.

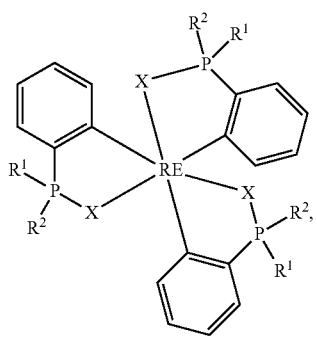

(1)

Note: It is better not to write an indicated double bond between P and X=CH2, because at the moment that CH2 coordinates according to the invention, the octet on the C atom is exceeded in case that there still is an indicated double bond. Two single bonds, as in modified FIG. 1), are equally applicable for both target groups (O as well as CH2).

Wherein

RE=Sc, Y, La, Ce, Pr, Nd, Pm, Sm, Eu, Gd, Tb, Dy, Ho, Er, Tm, Yb or Lu;

X=O, CRR';

$R^1$, $R^2$=phenyl;

R, R=independently of each other, H, alkyl with n=1

Preferably, if X=O, RE=Sc, Y, Lu or Yb in the homoleptic rare earth triaryl complex. If X=CH$_2$, RE=Sc, Y, Lu, Sm, Gd or Dy.

The homoleptic rare earth triaryl complex according to the invention is selected particularly preferably from the group consisting of:

[o-Sc(C$_6$H$_4$(C$_6$H$_5$)$_2$P=O)$_3$], [o-Y(C$_6$H$_4$(C$_6$H$_5$)$_2$P=O)$_3$], [o-Lu(C$_6$H$_4$(C$_6$H$_5$)$_2$P=O)$_3$],

[o-Yb(C$_6$H$_4$(C$_6$H$_5$)$_2$P=O)$_3$], [o-Y(C$_6$H$_4$(C$_6$H$_5$)$_2$P=CH$_2$)$_3$],

[o-Sc(C$_6$H$_4$(C$_6$H$_5$)$_2$P=CH$_2$)$_3$], [o-Lu(C$_6$H$_4$(C$_6$H$_5$)$_2$P=CH$_2$)$_3$],

[o-Dy(C$_5$H$_4$(C$_6$H$_5$)$_2$P=CH$_2$)$_3$], [o-Gd(C$_6$H$_4$(C$_6$H$_5$)$_2$P=CH$_2$)$_3$],

[o-Sm(C$_6$H$_4$(C$_6$H$_5$)$_2$P=CH$_2$)3].

The homoleptic rare earth triaryl complexes according to the invention are produced in that a triphenylphosphorane is reacted with a solvated rare earth metal halogenide or solvated organo rare earth metal complex in the temperature range of –30° C. to 120° C. The reaction occurs as a salt and/or hydrocarbon elimination. Advantageously, the process is carried out in situ by way of a one-pot-reaction. The conversion is achieved in aromatics, cyclic ethers or mixtures of these solvents.

The synthesis of homoleptic compounds is achieved by eliminating salt from the rare earth metal halogenide and three equivalents of the lithium salt (see FIG. I). A further possibility for preparing the same envisions eliminating hydrocarbon from the homoleptic organo metal precursors [SER$_3$(solv)$_n$] and three equivalents of the phosphorane (see FIG. II). Especially preferred is the one-pot method III (figure) that starts from the metal halogenide and three equivalents of the phosphorane. The deprotonation of the ortho-position is achieved in situ by adding a stoichiometrical quantity of a lithium base RLi (R=Me, CH$_2$SiMe$_3$, Bu, particularly: Ph).

FIG. 8: Possible synthesis paths to arrive at homoleptic rare earth metal complexes of ortho-metalated phenylphosphoranes

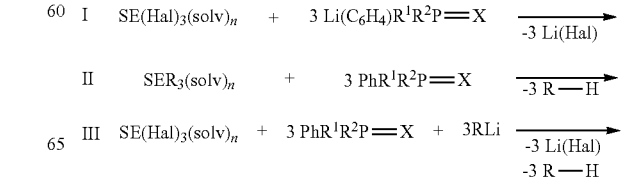

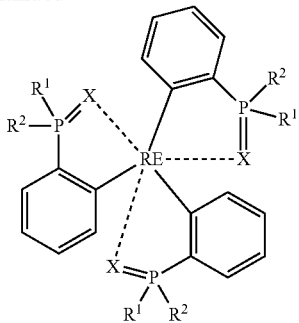

The described processes I-III therefore give access to a novel class of homoleptic chelate-stabilized phenylphosphorane complexes of rare earths. It was possible to obtain the trivalent cations of the metals samarium, gadolinium, dysprosium, yttrium, ytterbium, lutetium and scandium with triphenylphosporanes, such as triphenylphosphine oxide or triphenylmethylidene phosphorane.

It is particularly preferred to run the conversion in the temperature range of 0° C. to 60° C. The triphenylphosphorane is reacted with a solvated rare earth metal halogenide or solvated organo rare earth metal complex at a molar ratio of 3:1.

When the reaction occurs in form of a salt elimination, it is advantageous to add a quantity of a lithium base that is equimolar to the used triphenylphosphorane.

The homoleptic rare earth triaryl complexes are used as reagent or catalyst in organic reactions, as catalyst in ring-opening polymerizations in polyester production.

The homoleptic rare earth triaryl complexes are preferably also used as a precatalyst in the polymerization of olefins, particularly as a precatalyst in the polymerization of conjugated olefins.

After a first screening, the compounds show catalytic activity in the ring-opening polymerization of ε-caprolactone as well as, after the activation, in the diene polymerization of isoprene. With TLC measurements and NMR-spectroscopic analyses it was possible to document a high fraction of naturally-identical 1,4-cis-polyisoprene in the polymer.

The invention will be described in further detail below based on the embodiments that are provided for illustration.

Insofar as substances were used that react sensitively to water or oxygen, the SCHLENK technique was applied. The used glass instruments were heated in a high vacuum and filled with argon 4.8 by AIR LIQUIDE after cool-down. The argon that was used for this purpose was dried using a column that was filled with $P_4O_{10}$ granules and then with Solvona®. Weigh-ins and sample preparations for analytical studies, as well as the storage of oxygen- and/or hydrolysis-sensitive substances were done in glove boxes (Type MB 150 BG-I, BRAUN, Lab Master 130, by the BRAUN company) and under a nitrogen atmosphere. The used solvent, if needed, was dried and purified according to standard methods under a protective gas atmosphere.[2] The solvents were dehydrated, following pre-drying and destillation, in absorption columns over aluminum oxide/molecular sieve 3A/R3-11G catalyst (BASF).

Unless indicated otherwise, commercially available feed materials were purchased from the companies ACROS ORGANICS, SIGMA-ALDRICH and MERCK. Any purification that may have been carried out prior to using these substances is described in the associated synthesis protocols.

NMR Spectroscopy

The NMR spectra were recorded on these instruments: BRUKER Avance 300 ($^1$H (300.1 MHz), $^{13}$C (75.5 MHz), $^{31}$P (121.5 MHz), $^{19}$F (282.4 MHz)), BRUKER DRX 400 ($^1$H (400.0 MHz), $^{13}$C (100.6 MHz), $^{31}$P (161.9 MHZ), $^{11}$B (128.4 MHZ)), BRUKER DRX 500 ($^1$H (500.1 MHz), $^{13}$C (125.8 MHz), $^{31}$P (202.3 MHz)). All spectra were $^1$H-decoupled and, unless indicated otherwise, recorded at 298 K. The information as to the chemical shift δ was provided in ppm relative to a corresponding standard ($^1$H & $^{13}$C: TMS, $^{31}$P: 85% $H_3PO_4$, $^{19}$F: $CFCl_3$, $^{11}$B: 15% solution of $[BF_3Et_2O]$ in $CDCl_3$). The coupling constant $^nJ_{AB}$ describes the coupling of two nuclei A and B with ½ nucleic spin over n bonds. The $^{31}$P-NMR spectra were calibrated relative 85% phosphoric acid as internal standard. The calibration of the $^1$H and $^{13}$C spectra was done by residual proton and solvent signals of the corresponding dedeuterized solvent ($^1$H/$^{13}$C:$C_6D_6$ (7.16/128.02 ppm), THF-$d_8$ (3.58/67.40 ppm), toluene-$d_8$: (2.08/20.5 ppm). The multiplicity of the signals is indicated by: s=singlet; d=doublet; dd=doublet of doublet; t=triplet; dt=doublet of triplet; q=quadruplet; quin=quintet; sept=septet, m=multiplet; br=wide signal. In the analysis of the NMR spectra, the nomenclature for the position was selected as shown below in FIG. 9 on the twice-substituted phenyl ring.

FIG. 9: Identification of the positions on different aromatics (M = metal); elemental analysis

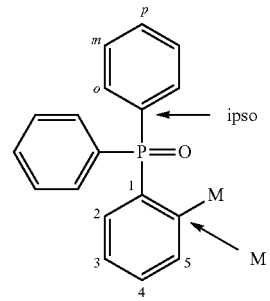

The content of the elements C, H and N was established with the instrument CHN-Rapid by HERAEUS. Samples of water- and air-sensitive substances were filled inside the glove box in cold-welded zinc crucibles. The chloride content was established argentometrically. The information is provided in weight-percent, as in the elemental analysis.

Analysis of the Crystalline Structure

The monocrystal x-ray diffractograms were taken on surface area detector systems (IPDS I, IPDS II by STOE) at the Department of Chemistry of the Philipps-University of Marburg by Dr. K. Harms, G. Geisseler and R. Riedel. A standard graphite monochromator (Mo-Ka-radiation, λ=71.073 pm) was employed. The data were gathered with IPDS Software X-Area by the company STOE. The collected data were integrated in the service department, while we did the dissolution and purification steps ourselves. Absorption corrections were done semi-empirically, insofar as possible, using multi-scans. Direct methods were used for the structural solution (Sir-92, Sir-97, Sir-2002, Sir-2004 and SHELXS-86). To refine results, the method of the smallest error square was employed (SHELXL-97). With the exception of the hydrogen atoms, the positions of all atoms were anisotropically refined. Hydrogen atoms that are involved in the structural formation of hydrogen bridge formations or whose presence has a determinative influence on the molecular structure, were localized in the difference Fourier map and isotropically refined. The Diamond program was used for preparing the structures. The results of the crystal structure analyses are compiled in the crystallographic annex.

Infrared Spectroscopy

The IR spectra were recorded on an ATR-FT-IR spectrometer of the Alpha-P type BRUKER. The measurements were taken inside the glove box in substance. The absorption bands are indicated in $cm^{-1}$. The absorption band characteristics are described as follows: w=weak, m=medium, s=strong, br=broad, v=reciprocal wavelength in $cm^{-1}$.

Mass Spectrometry

Mass spectra of the electron impact (EI) and field desorption (FD) were recorded with the spectrometer FINNIGAN MAT CH7 (electron energy=70 eV). Air- and/or hydrolysis-sensitive samples were prepared inside the glove box. The indicated m/z values relate to the isotopes with the greatest natural frequency by which they are encountered. The most important fragments are noted.

Gel Permeation Chromatography (GPC)

Molecular weights and polydispersities were established by gel permeation chromatography relative to polystryrol standards in THF at 20° C. The GPC measurement of the polyisoprene was taken in pure THF, while 5% trifluoroascetic acid (v/v) was added to THF as eluent for the measurement of the polyesters.

Thermogravimetric Analysis (TGA) & Differential Scanning Calorimetric Analysis (DSC)

The thermogravimetric analysis was done on a TGA/SDTA 851 instrument (by METTER TOLEDO). For the TGA measurements, the sample was weighed in into a 70 μL aluminum oxide crucible, each time with the ultra-micro scale integrated in the instrument. The DSC measurements of the polymer samples were taken with a DSC 821 instrument by METTER TOLEDO. To this end, 6 to 8 mg of the substance were weighed in each time in a 40 μL aluminum crucible. The lid of the sealed crucible was pierced with a hole to ensure equalization of pressure. The used temperature program had two cycles. The samples were measured inside a temperature range of −90 to 60° C. with heating rates of 10 K/min.

EXAMPLE 1

[o-Sc($C_6H_4$($C_6H_5$)$_2$P=O)$_3$]. 184 mg [ScCl$_3$(thf)$_3$] (0.5 mmol) was weighed in together with 418 mg triphenylphosphine oxide (1.5 mmol) to which is added 10 mL THP. The suspension was stirred for 30 minutes at room temperature. No formation of a coarse flaky solid occurred.

The substance was then cooled to 0° C., 0.75 mL of a PhLi solution (20% solution in Bu$_2$O, 1.5 mmol) was added, and stirring was continued for another two hours at the given temperature. The suspension slowly turned a brown color, wherein the major part of the solid material became dissolved. The solvent was removed completely, and the obtained brown solid was taken up in benzene and filtered with Chelite®. The benzene was removed in a fine vacuum, and the product was recrystallized from THP at −30° C. After decanting, the substance was dried in a fine vacuum. 118 mg (27%) of a beige-brown-colored solid material was obtained.

$^1$H-NMR (300.1 MHz, $C_6D_6$): δ=6.83-7.06 (m, 8H, H$_o$, H$_p$, H$_2$, H$_4$), 7.67-7.74 (m, 5H, H$_m$, H$_3$), 8.24 (d, 1H $^3J_{HH}$=6.99 Hz, H$_5$) ppm $^{13}$C-NMR (75.5 MHz, $C_6D_6$): δ=124.5 (d, $^3J_{CP}$=14.4 Hz, C$_3$), 128.3 (d, $^2J_{CP}$=12.1 Hz, C$_o$), 129.2 (d, $^4J_{CP}$=4.0 Hz, C$_4$), 131.4 (d, $^4J_{CP}$=2.4 Hz, C$_p$), 132.7 (d, $^3J_{CP}$=10.4 Hz, C$_m$), 133.2 (d, $^1J_{CP}$=97.7 Hz, C$_{ipso}$), 140.2 (d, $^3J_{CP}$=24.8 Hz, C$_5$), 139.7 (d, $^1J_{CP}$=119.5 Hz, C$_1$), (C$_{Sc}$ could not be observed) ppm.

$^{31}$P-NMR (121.5 MHz, $C_6D_6$): 5=43.4 ppm

Elemental analysis $C_{54}H_{42}O_3P_3Y$ (876.79 g/mol); calculated C, 73.97; H, 4.83; N, 0.0. found: C, 72.54; H, 5.37; N, 0.0.

IR spectroscopy (v/$cm^{-1}$): 3011(br), 1483(w), 1436(s), 1415(w), 1222(w), 1195(w), 1131(s), 1119(s), 1079(s), 1063(s), 1025(m), 998(m), 748(w), 721 (s), 692(s), 628(s), 537(s), 463(s), 443(s), 414(s)

EXAMPLE 2

[o-Y($C_6H_4$($C_6H_5$)$_2$P=O)$_3$]. 410 mg [YCl$_3$(thf)$_3$] (1.0 mmol) was weighed in together with 835 mg triphenylphosphine oxide (3.0 mmol) to which was added 15 mL THP. The suspension was stirred for 30 min at RT during which time the fine crystalline substances turned into a coarse flaky solid material. The substance was then cooled to 0° C., 1.5 mL of a PhLi solution (20% solution in Bu$_2$O, 3.0 mmol) was added, and the substance was stirred for two more hours at the given temperature. The suspension increasingly turned a brown color, wherein the solid material became dissolved for the most part. The solvent was then removed completely and the obtained brown solid material was taken up in benzene and filtered with Chelite®. The filtrate was evaporated to one third of the volume, and 10 mL pentane was added to this causing a beige-colored solid material to precipitate from the dark-brown solution. The suspension was stirred for 20 minutes and then filtered. The solid material was dried under a fine vacuum. 497 mg (54%) of a light-brown solid material was obtained.

Note: Recrystallization from THP failed, although several attempts were made.

$^1$H-NMR (300.1 MHz, $C_6D_6$): δ=6.81-6.86 (m, 5H, H$_o$, H$_2$), 7.27-7.33 (m, 3H, H$_p$, H$_4$), 7.63-7.69 (m, 5H, H$_m$, H$_3$), 8.69 (d, 1H, $^3J_{HH}$=6.88 Hz, H$_5$) ppm No usable $^{13}$C-NMR spectrum could be obtained.

$^{31}$P-NMR (121.5 MHz, $C_6D_6$): δ=42.0 (d, $^3J_{YP}$=9.18 Hz) ppm

Elemental analysis $C_{54}H_{42}O_3P_3Y$ (920.74 g/mol); calculated: C, 70.44; H, 4.60. found: C, 67.22; H, 5.98.

IR-spectroscopy (v/$cm^{-1}$): 3024(w, br), 2936(w, br), 2844 (w, br), 1483(w), 1435(m), 1194(w), 1131(w), 1118(m), 1080(m), 1063(w), 1047(w), 1025(w), 997(w), 871(w), 747 (w), 720(m), 691(m), 627(w), 537(s), 460(m), 449(m)

Crystallographic data: trigonal, P 2$_1$/a, a=14.4820(3) Å, b=17.7836(4) Å, c=19.3122(4) Å, α=90°, β=94.101(2)°, λ=90°, V=4960.97(18) Å$^3$, Z=4, D$_c$=1.348 mg/m$^3$, μ=1.320 mm$^{-1}$,

F(000)=2088

EXAMPLE 3

[o-Lu($C_5H_4$($C_6H_5$)$_2$P=O)$_3$]. 249 mg [LuCl$_3$(thf)$_3$] (0.5 mmol) was weighed in together with 418 mg triphenylphosphine oxide (1.5 mmol) to which 10 mL THP was added. The suspension was stirred for 30 min at RT, during which time a coarse flaky solid material formed from the initially fine crystalline material. The substance was then cooled to 0° C. and 0.75 mL PhLi solution (20% solution in Bu$_2$O, 1.5 mmol) was added, stirring was continued for two more hours at the given temperature. The suspension increasingly turned to a brown color during which time the majority of the solid material became dissolved. The solvent was removed completely and the obtained brown solid material was taken up in benzene, and then filtered with Chelite®. The benzene was removed, and the product was recrystallized from THP at −30° C. After decanting, drying occurred under a fine vacuum. 90 mg (18%) of a beige-brown-colored solid material was obtained.

$^1$H-NMR (300.1 MHz, $C_6D_6$): δ=6.81-6.87 (m, 5H, $H_o$, $H_2$), 7.30-7.35 (m, 3H, $H_p$, $H_4$), 7.65-7.71 (m, 5H, $H_m$, $H_3$), 8.61 (d, 1H, $^3J_{HH}$=6.37 Hz, $H_5$) ppm $^{13}$C-NMR (75.5 MHz, $C_6D_6$): δ=124.6 (d, $^3J_{CP}$=14.5 Hz, $C_3$), 128.3 (d, $^2J_{CP}$=11.5 Hz, $C_o$), 128.8 (s, $C_2$), 129.2 (d, $^4J_{CP}$=4.2 Hz, $C_4$), 131.4 (d, $^4J_{CP}$=2.5 Hz, $C_p$), 132.6 (d, $^3J_{CP}$=10.4 Hz, $C_m$), 133.7 (d, $^1J_{CP}$=97.9 Hz, $C_{ipso}$), 141.5 (d, $^3J_{CP}$=25.5 Hz, $C_5$), 141.0 (d, $^1J_{CP}$=119.2 Hz, C,), 206.9 (d, $^2J_{CP}$=40.4 Hz, $C_{Lu}$) ppm
[illegible]

Elemental analysis $C_{54}H_{42}O_3P_3LU$ (1006.80 g/mol); calculated C, 64.42; H, 4.20. found: C, 63.77; H, 4.55.

IR spectroscopy (v/cm$^{-1}$): 3011(w, br), 1483(w), 1436(m), 1415(w), 1222(w), 1195(w), 1131(m), 1119(m), 1079(m), 1063(m), 1025(w), 998(w), 748(w), 721(m), 692(m), 628 (w), 537(s), 463(m), 443(m), 414(m)

Crystallographic data: triclinic, P-1, a=11.4691(3) Å, b=14.3439(3) Å, c=19.7816(3) Å, α=93.949(2)°, β=90.486(2)°, γ=96.701(2)°, V=3223.95(12) Å$^3$, Z=2, $D_c$=1.392 mg/m$^3$, μ=1.660 mm$^{-1}$, F(000)=1396

EXAMPLE 4

[o-Yb($C_6H_4(C_6H_5)_2$P=O)$_3$]. 248 mg [YbCl$_3$(thf)$_3$] (0.5 mmol) was weighed in together with 418 mg triphenylphosphine oxide (1.5 mmol) to which was added 10 mL THP. The suspension was stirred for 30 min at RT, and during this time a coarse flaky solid material formed from the initially fine crystalline material. The substance was then cooled to 0° C. and 0.75 mL PhLi solution (20% solution in Bu$_2$O, 1.5 mmol) was added to this, and stirring was continued for two more hours at the given temperature. The suspension increasingly turned a brown color, wherein the majority of the solid material became dissolved during this time. The solvent was removed completely, and the obtained brown solid material was taken up in benzene and filtered with Chelite®. The benzene was then removed, and the product was recrystallized from THP at −30° C. After decanting, the substance was dried in a fine vacuum.

126 mg (25%) of a beige-brown solid material was obtained.

NMR spectroscopic analysis is not possible due to marked paramagnetism.

Elemental analysis $C_{54}H_{42}O_3P_3$Yb (1004.87 g/mol); calculated C, 64.54; H, 4.21. found: C, 63.82; H, 4.62.

IR spectroscopy (v/cm$^{-1}$): 3025(w, br), 2926(w, br), 2844 (w, br), 1483(w), 1435(m), 1194(w), 1131(w), 1117(m), 1082(m), 1063(w), 1047(w), 1025(w), 997(w), 871(w), 747 (w), 720(m), 690(w), 627(w), 537(s), 460(m), 446(m)

EXAMPLE 5

Poly-ε-caprolactone. The polymerization of ε-caprolactone always occurred at RT in toluene. Selected catalyst/monomer ratio of 1:150

A solution of the needed catalyst quantity was prepared in 20 mL toluene to which was quickly added the corresponding quantity of ε-caprolactone. Typically, an increase in viscosity was quickly noticed. After a reaction time of one hour, the reaction mixture in 200 mL was poured over methanol that had been cooled to 0° C., and the polymer precipitated. The precipitate was dried overnight at 40° C. The sample preparation for the GPC measurement included renewed dissolution in THF, followed by filtration with a 0.45 μm syringe filter and another precipitation in 100 mL over methanol that cooled to 0° C. The polymer was filtered off again and dried at 40° C. The results of the experiments are compiled in Table 1.

TABLE 1

Summary of the polymerization results for ε-caprolactone

| Catalyst | Yield/g | Yield/% | Polydispersity D | Chain length $M_w$/g/mol |
|---|---|---|---|---|
| Example 1 | 0.703 | 65 | 2.96 | 163260 |
| Example 2 | 1.087 | 100 | 1.49 | 49733 |
| Example 3 | 1.044 | 97 | 2.98 | 89342 |

Test for living polymerization. Using the example [o-Y ($C_6H_4(C_6H_5)_2$P=O)$_3$], the goal was to demonstrate that, in the case of the ring-opening polymerization of ε-caprolactone with this substance class, there was in fact a living polymerization. The chosen starting ratio of catalyst/monomer was 1:150.

46.4053 mg [o-Y($C_6H_4(C_6H_5)_2$P=O)$_3$]. (0.0504 mmol) was dissolved in 40 mL toluene and 0.8 mL ε-caprolactone (7.5696 mmol) was added quickly at RT. After one hour, 10 mL of the reaction mixture was removed and added in 200 mL on methanol that had been cooled to 0° C. The precipitated polymer was filtered off and underwent a work-up. Another 10 mL toluene was added to the remaining reaction mixture to reduce the viscosity. Then, calculated for the catalyst quantity still remaining in the reaction vessel, another 150 equivalents of E-caprolactone (0.6 mL, 5.6772 mmol) was added, and the substance was stirred for another hour. This process was repeated twice. After each sample-taking, the catalyst/monomer ratio was increased by 150 equivalents. The results are compiled in Table 2.

TABLE 2

Result of the tests for living polymerization

| Sample Catalyst: | Yield/mg | Yield/% | Polydispersity D | Chain length $M_w$/g/mol | monomer ratio |
|---|---|---|---|---|---|
| Sample 1 | 56 | 26 | 1.20 | 15185 | 1:150 |
| Sample 2 | 190 | 44 | 1.36 | 21892 | 1:300 |
| Sample 3 | 318 | 45 | 1.45 | 23682 | 1:450 |
| Sample 4 | 340 | 42 | 1.50 | 26700 | 1:600 |

Poly-L-lactide (A). Polymerization of L-lactide was always done at room temperature in toluene. The ratio of catalyst/monomer was selected as 1:150. The needed quantity of catalyst was dissolved in 10 mL toluene and 3 mL of a solution of (L,L)-dilactide in THF (c=0.99315 mol/L, 2.9795 mmol) was quickly added. The substance was stirred for two hours at RT, then the reaction mixture was poured over weak HCl-acidic methanol and the polymer precipitated. The precipitate was dried overnight at 40° C. The sample preparation for the GPC measurement was done by dissolving the substance once more in THF, followed by filtration with a 0.45 μm syringe filter and another precipitation in 100 mL on methanol that had been cooled to 0° C. The polymer was filtered off again and dried at 40° C. The results from the experiments are compiled in Table 3.

TABLE 3

Summary of the polymerization results of L-lactide

| Catalyst | Yield/mg | Yield/% | Polydispersity D | Chain length $M_w$ |
|---|---|---|---|---|
| Compound | 317 | 73 | — | 7212 |
| 4 | 244 | 57 | 1.49 | 10527 |
| Compound | 376 | 87 | 1.54 | |

COMPARISON EXAMPLE 1

Poly-L-lactide (B). 40.000 mg [o-Sn($C_6H_4(C_6H_5)_2$P=O)$_2$] (0.05941 mmol, 1 eq) was dissolved in 5.0 mL toluene and added to a solution of 2.569 g (L,L)-dilactide (0.01782 mmol, 300 eq) in 10.0 mL toluene. The reaction mixture was heated for 24 hours to 100° C. After cooling down, the reaction solution was poured in 200 mL weak HCl-acidic methanol, and the polymer precipitated. The precipitate was then dried overnight at 40° C. To prepare the sample for the GPC measurement, it was dissolved once more in THF, followed by filtration with a 0.45 μm syringe filter and another precipitation in 100 mL on methanol cooled to 0° C. The polymer was filtered off again and dried at 40° C. 1.84 g poly-L-lactide (72%) was obtained.

GPC (THF (+TFA 5 vol %): D=1.45; $M_w$=117180 g/mol.

EXAMPLE 6

Polyisoprene. 0.01 mmol of the precatalyst was provided in 7.8 mL chlorobenzene, and 1.0 mL isoprene (10 mmol) was added to this. 8.012 mg [PhNHMe$_2$][B($C_6F_5$)$_4$] was then added after having been dissolved in 1.0 mL chlorobenzene. After 15 minutes, 0.2 mL of a solution of TIBAL in toluene (c=0.0581 mol/L, 0.1164 mmol) was added, and the reaction mixture was stirred for 24 hours. To quench the polymerization, weakly HCl-acidic methanol was used with a bit of 2,4-ditertbutyl-4-methyl-phenol. After expiration of the reaction time, the weakly viscous reaction solution was poured in 100 mL of the aforementioned methanolic solution, which caused the polymer to precipitate. The precipitate was then dried under a fine vacuum for ten hours. The sample preparation for the GPC measurement was done by dissolving the substance once again in 10 mL dichloromethane, followed by filtration with a 0.45 μm syringe filter and another precipitation in 100 mL of the aforementioned methanolic solution. The polymer was dried once more under a fine vacuum. The ratio of the different possible coupling modes was established by a curve analysis of the methyl proton signals. The signal for 1,2-coupled polyisoprene was not observed. The $^1$H-NMR spectra were recorded in CDCl$_3$. The results are compiled in Table 4.

TABLE 4

Summary of the polymerization results of isoprene

| Catalyst | Yield/mg | Yield/% | Polydispersity D | Chain length $M_w$ | Glass point/ ° C. | Coupling/ 1.4 cis: 1.4 trans: |
|---|---|---|---|---|---|---|
| Expl 1 | 340 | 50 | —* | 63000* | −62.1 | 92:2:6 |
| Expl 2 | 650 | 96 | 1.69 | 44498 | −62.2 | 75:6:19 |

*Regarding Example 1, a multimodal distribution was determined by the GPC measurement. The polydispersity can therefore not be established; $M_w$ was determined graphically from the elugram of the measurement.

EXAMPLE 7

The synthesis of the homoleptic triphenylmethylidene phosphorane complexes will be described below in an exemplary manner for [o-Y($C_6H_4(C_6H_5)_2$P=CH$_2$)$_3$]. The syntheses as well as the growing of monocrystals in Examples 8 to 12 were done analogously.

[o-Y($C_6H_4(C_6H_5)_2$P=CH$_2$)$_3$]. 206 mg [YCl$_3$(thf)$_3$] (0.5 mmol) was weighed in together with 414 mg ($C_6H_5$)$_3$P=CH$_2$ (1.5 mmol) and dissolved in 10 mL THF. A yellow solution formed. After 15 minutes, the reaction mixture was cooled down to 0° C. and 0.75 mL PhLi solution (20% ig in Bu$_2$O, 1.5 mmol) was slowly dropped in. After the completed addition, the reaction solution was slowly heated to RT; in regular one-hour intervals, samples 0.5 mL each were taken and tested via $^{31}$P-NMR spectroscopy. The solution increasingly turned an orange color, then a dark-brown. After six hours, it was confirmed with $^{31}$P-NMR spectroscopy that the conversion was complete. The solvent was then removed in a fine vacuum, and the residue was taken up in toluene, and then filtered with Celite®. The filtrate was evaporated to half of the volume, and 1 mL pentane was added. After the crystallization at −30° C., decanting and drying in a fine vacuum, it was possible to isolate 288 mg (63%) of a yellow, fine-crystalline solid material. By superimposing a saturated layer of a toluene solution with pentane (ratio 1:1 (V:V)), it was possible to obtain suitable monocrystals for the crystalline structural analysis.

$^1$H-NMR (300.1 MHz, C$_6$D$_6$): δ=0.76 (dd, 2H, $^2J_{HH}$=9.35 Hz, $^2J_{HY}$=0.92 Hz, CH$_2$), 6.85-6.91 (m, 5H, H$_o$, H$_2$), 6.96-7.01 (m, 3H, H$_p$, H$_4$), 7.32-7.38 (m, 5H, H$_m$, H$_3$), 8.71 (d, 1H, $^2J_{HH}$=6.59 Hz, H$_5$) ppm $^{13}$C-NMR (75.5 MHz, C$_6$D$_6$): δ=14.1 (dd, $^1J_{CP}$=41.1 Hz, $^1J_{CP}$=14.3 Hz, CH$_2$), 124.2 (d, $^2J_{CP}$=13.0 Hz, C$_0$), 130.4 (d, $^4J_{CP}$=2.6 Hz, C$_r$), 130.9 (d, $^4J_{CP}$=1.3 Hz, C$_4$), 132.0 (d, $^2J_{CP}$=9.5 Hz, C$_2$), 132.6 (d, $^3J_{CP}$=9.6 Hz, C$_3$), 132.7 (d, $^3J_{CP}$=9.2 Hz, C$_m$), 134.3 (d, $^1J_{CP}$=69.8 Hz, C$_{ipso}$), 139.1 (dd, $^1J_{CP}$=112.6, $^2J_{CP}$=2.0 Hz, C$_1$), 140.3 (d, $^3J_{CP}$=27.8 Hz, C$_5$), 204.1 (dd, $^2J_{CP}$=52.8 Hz, $^1J_{CP}$=33.4 Hz, C$_y$) ppm $^{31}$P-NMR (121.5 MHz, C$_6$D$_6$): δ=26.7 (d, $^2J_{PT}$=4.0 Hz) ppm Elemental analysis C$_{57}$H$_{48}$P$_3$Y (914.82 g/mol); calculated C, 74.84; H, 5.29. found: C, 73.19; H, 5.50.

IR spectroscopy (v/cm$^{-1}$): 2970(w, br), 1433(m), 1413(w), 1102(m), 1070(m), 998(w), 868(m), 741 (m), 720(m), 690 (m), 665(m), 625(m), 520(s), 491 (m), 455(m), 433(w), 404 (w)

Crystallographic data: trigonal, R-3, a=20.085(5) Å, b=20.085(5) Å, c=20.610(5) Å, α=β=90.000(5)°, λ=120.000 (5)°, V=8947(4) Å$^3$, Z=6, D$_c$=1.358 mg/m$^3$, μ=1.450 mm$^{-1}$, F(000)=3792

EXAMPLE 8

[o-Sc($C_6H_4(C_6H_5)_2$P=CH$_2$)$_3$]. The synthesis followed a 0.5 mmol scale. The reaction time was 24 hours. Following recrystallization, 322 mg (74%) of a yellow, fine-crystalline solid material was obtained.

$^1$H-NMR (300.1 MHz, C$_6$D$_6$): δ=1.01 (d, 2H, $^2J_{HH}$=9.58 Hz, CH$_2$), 6.90-7.05 (m, 5H, H$_o$, H$_2$), 7.29-7.35 (m, 3H, H$_p$, H$_4$), 7.61-7.66 (m, 5H, H$_m$, H$_3$), 8.41 (d, 1H, $^2J_{HH}$=6.76 Hz, H$_5$) ppm $^{13}$C-NMR (75.5 MHz, C$_6$D$_6$): 12.8 (d, $^1J_{CP}$=39.2 Hz, CH$_2$), 124.1 (d, $^2J_{CP}$=12.9 Hz, C$_0$), 128.4 (d, $^3J_{CP}$=11.4 Hz, C$_2$), 130.4 (d, $^4J_{CP}$=2.3 Hz, C$_p$), 130.6 (d, $^4J_{CP}$=2.4 Hz, C$_4$), (d, $^2J_{CP}$=9.7 Hz, C$_m$), 132.7 (d, $^3J_{CP}$=9.0 Hz, C$_3$), 134.3 (d, $^1J_{CP}$=69.2 Hz, C$_{ipso}$), 137.7 (d, $^1J_{CP}$32 113.2 Hz, C,), 140.7 (d, $^3J_{CP}$=27.3 Hz, C$_5$), (C$_{Sc}$ would not be observed) ppm $^{31}$P-NMR (121.5 MHz, C$_6$D$_6$): δ=31.1 (s) ppm Elemental analysis C$_{57}$H$_{48}$P$_3$Sc (870.87 g/mol); calculated: C, 78.61; H, 5.56. found: C, 78.68; H, 6.05.

IR spectroscopy (v/cm$^{-1}$): 3020(w, br), 2946(w, br), 1480 (w), 1434(m), 1414(w), 1102(m), 1073(m), 1027(w), 998 (w), 970(w), 931(w), 868(m), 749(m), 737(s), 711(m), 691(s), 630(m), 532(m), 513(s), 452(s), 434(m), 412(m)

Crystallographic data: trigonal, R-3, a=19.9558(15) Å, b=19.9558(15) Å, c=25.421(2) Å, α=β=90°, γ=120°, V=8767(12) Å$^3$, Z=6, D$_c$=1.094 mg/m$^3$, μ=0.244 mm$^{-1}$, F(000)=3036

EXAMPLE 9

[o-Lu(C$_6$H$_4$(C$_6$H$_5$)$_2$P=CH$_2$)$_3$]. The synthesis followed a 0.5 mmol scale. The reaction time was 24 hours. Following recrystallization, 345 mg (69%) of the yellow crystalline product was obtained.

$^1$H-NMR (300.1 MHz, C$_5$D$_6$): δ=0.73 (d, 1H, $^2J_{HH}$=9.61 Hz, CH$_2$), 6.87-6.92 (m, 5H, H$_0$, H$_2$), 6.98-7.07 (m, 3H, H$_p$, H$_4$), 7.28-7.34 (m, 5H, H$_m$, H$_3$), 8.66 (d, 1H, $^3J_{HH}$=6.79 Hz, H$_5$) ppm $^{13}$C-NMR (75.5 MHz, C$_6$D$_6$): δ=17.2 (d, $^1J_{CP}$=40.0 Hz, CH$_2$), 124.1 (d, $^2J_{CP}$=13.1 Hz, C$_0$), 130.4 (d, $^4J_{CP}$=2.5 Hz, C$_p$), 130.5 (d, $^4J_{CP}$=2.8 Hz, C$_4$), 132.6 (d, $^2J_{CP}$=6.0 Hz, C$_2$), 132.7 (d, $^3J_{CP}$=5.6 Hz, C$_3$), 134.4 (d, $^3J_{CP}$=12.2 Hz, C$_m$), 134.7 (d, $^1J_{CP}$=69.9 Hz, C$_{ipso}$), 139.5 (d, $^1J_{CP}$=112.1 Hz, C$_1$), 141.2 (d, $^3J_{CP}$=27.6 Hz, C$_5$), 211.5 (d, $^2J_{CP}$=52.7 Hz, Cu) ppm $^{31}$P-NMR (121.5 MHz, C$_6$D$_6$): δ=29.6 (s) ppm Elemental analysis C$_{57}$H$_{48}$P$_3$Lu (1000.88 g/mol); calculated: C, 66.40; H, 4.83. found: C, 66.44; H, 5.50.

IR spectroscopy (v/cm$^{-1}$): 3011(w, br), 2949(w, br), 1434 (m), 1412(w), 1174(w), 1113(w), 1099(m), 1070(m), 1027 (w), 998(w), 979(w), 927(m), 868(m), 730(m), 712(m), 691 (s), 627(w), 558(w), 512(s, br), 464(m), 447(m), 408(m)

Crystallographic data: trigonal, R-3, a=20.0214(8) Å, b=20.0214(8) Å, c=25.5605(13) Å, α=β=90°, γ=120°, V=8873.4(7) Å$^3$, Z=6, D$_c$=1.124 mg/m$^3$, p=1.779 mm$^{-1}$, F(000)=3036

EXAMPLE 10

[o-Dy(C$_6$H$_4$(C$_6$H$_5$)$_2$P=CH$_2$)$_3$]. The synthesis followed a 0.5 mmol scale. The reaction time was 6 hours. Following recrystallization, 351 mg (71%) of the desired product were isolated.

Elemental analysis C$_{57}$H$_{48}$P$_3$Dy (988.41 g/mol); calculated: C, 69.26; H, 4.98. found: C, 69.63; H, 5.25.

IR spectroscopy (v/cm$^{-1}$): 2947(w, br), 1433(m), 1102(w), 1069(w), 1026(w), 997(w), 921 (w), 871 (w), 742(w), 716 (m), 691 (s), 625(w), 521 (s), 492(m), 456(w), 439(w), 404 (w)

Crystallographic data: triclinic, P-1, a=10.4014(4) Å, b=16.8153(7) Å, c=18.5046(7) Å, α=113.568(3)°, β=99.621 (3)°, γ=92.223(3)°, V=2904.8(2) Å$^3$, Z=2, D$_c$=1.281 mg/m$^3$, p=1.407 mm$^{-1}$, F(000)=1145

EXAMPLE 11

[o-Gd(C$_6$H$_4$(C$_6$H$_5$)$_2$P=CH$_2$)]. The synthesis followed a 0.5 mmol scale. The reaction time was six hours. Following recrystallization, 275 mg (56%) of the yellow crystalline target compound was obtained.

Elemental analysis C$_{57}$H$_{48}$P$_3$Gd (983.16 g/mol); calculated: C, 69.63; H, 4.92. found: C, 60.14; H, 4.63.

IR spectroscopy (v/cm$^4$): 2968(w, br), 1433(m), 1413(w), 1102(m), 1068(m), 1026(w), 997(w), 913(w), 872(m), 741 (m), 720(m), 690(s), 624(m), 519(s), 489(s), 455(m), 437(m)

Crystallographic data triclinic, P-1, a=10.4014(4) Å, b=16.8153(7) Å, c=18.5046(7) Å, α=13.568(3)°, β=99.621 (3)°, γ=92.223(3)°, V=2904.8(2) Å$^3$, Z=2, D$_c$=1.282 mg/m$^3$, μ=1.263 mm$^{-1}$, F(000)=1148

EXAMPLE 12

[o-Sm(C$_6$H4(C$_6$H5)2P=CH2)3] The synthesis followed a 0.5 mmol scale. The reaction time was 3 hours. Following recrystallization, 376 mg (77%) of the compound 13 was isolated.

$^1$H-NMR (300.1 MHz, C$_6$D$_6$): δ=1.11 (d, 2H, $^2J_{HH}$=7.68 Hz, CH$_2$), 6.55-6.60 (m, 4H, H$_0$), 6.69-6.82 (m, 7H, H$_m$, H$_p$), 7.01-7.05 (m, 1H, H$_3$), 7.71-7.77 (m, 1H, H$_4$), 8.01-8.05 (m, 1H, H$_2$), 12.46 (d, 1H, $^3J_{HH}$=6.25 Hz, H$_5$) ppm $^{13}$C-NMR (75.5 MHz, C$_6$D$_6$): δ=−4.3 (d, $^2J_{CP}$=100.2 Hz, CH$_2$), 124.2 (d, $^2J_{CP}$=13.0 Hz, C$_2$), 128.5 (d, $^3J_{CP}$=17.2 Hz, C$_3$), 130.4 (d, $^4J_{CP}$=2.5 Hz, C$_p$), 130.6 (d, $^4J_{CP}$=2.7 Hz, C$_4$), 132.6 (d, $^2J_{CP}$=9.5 Hz, C$_o$), 132.7 (d, $^3J_{CP}$=8.4 Hz, C$_m$), 134.3 (d, $^1J_{CP}$=69.5 Hz, C$_{ipso}$), 139.1 (d, $^1J_{CP}$=112.6 Hz, C$_1$), 140.3 (d, $^3J_{CP}$=27.9 Hz, C$_5$), 204.1 (d, $^2J_{CP}$=52.6 Hz, C$_{sm}$) ppm $^{31}$P-NMR (121.5 MHz, C$_6$D$_6$): δ=24.0 (s, br) ppm Elemental analysis C$_{57}$H$_{45}$P$_3$Sm (976.27 g/mol); calculated: C, 70.12; H, 4.96. found: C, 69.90; H, 4.87.

IR spectroscopy (v/cm$^{-1}$): 2969(w, br), 1433(m), 1130(w), 1103(m), 1069(w), 1026(w), 997(w), 872(m), 741(m), 721 (m), 691(s), 656(m), 624(m), 517(s), 490(s), 454(m), 431(m), 414(m)

Crystallographic data: triclinic, P-7, a=10.4202(5) Å, b=16.8904(8) Å, c=18.5499(9) Å, α=113.512(4)°, β=99.832 (4)°, γ=92.138(4)°, V=2929.6(2) Å$^3$, Z=2, D$_c$=1.316 mg/m$^3$, μ=1.125 mm'$^1$, F(000)=1194

EXAMPLE 13

Poly-ε-caprolactone. The polymerization of ε-caprolactone always occurred at RT in toluene. The catalyst/monomer ratio was selected as 1:500.

A solution of the needed quantity of catalyst was prepared in 20 mL toluene to which was quickly added the corresponding quantity of ε-caprolactone. Typically, it was possible to observe a very rapid increase in viscosity. After an hour of reaction time, the reaction mixture was poured in 200 mL on methanol that had been cooled to auf 0° C. causing the polymer to precipitate. Said precipitate dried overnight at 40° C. The sample preparation for the GPC measurement was done by a further dissolution in THF, followed by filtration with a 0.45 μm syringe filter and another precipitation in 100 mL on methanol cooled to 0° C. The polymer was filtered off again and dried at 40° C. The results of the experiments are compiled in Table 5.

TABLE 5

Summary of the polymerization results of ε-caprolactone

| Catalyst | Yield/g | Yield/% | Polydispersity D | Chain length M$_w$ |
|---|---|---|---|---|
| Exp. 7 | 1.766 | 75 | 2.54 | 45117 |
| Exp. 8 | 2.330 | 82 | 1.74 | 47713 |

EXAMPLE 14

Polyisoprene. 0.01 mmol of the precatalyst was provided in 7.8 mL chlorobenzene and 1.0 mL isoprene (10 mmol) was added to this. After this, 8.012 mg [PhNHMe$_2$][B(C$_6$F$_5$)$_4$] was added, after it had been dissolved in 1.0 mL chlorobenzene. After 15 minutes, 0.2 mL of a solution of TIBAL in toluene (c=0.0581 mol/L, 0.1164 mmol) was added, and the reaction mixture was stirred for 24 hours. Weak HCl-acidic methanol with some 2,4-ditertbutyl-4-methyl-phenol was used to quench the polymerization. After the expiration of the reaction time, the weakly viscous reaction solution was poured in 100 mL of the aforementioned methanolic solution causing the precipitation of the polymer. The same was dried in a fine vacuum for ten hours. The sample preparation for [text missing] was done with a 0.45 μm syringe filter, and again precipitation in 100 mL of the aforementioned methanolic solution. The precipitate was once again dried in a fine vacuum. The ratio of the different possible coupling modes was determined by a curve analysis of the methyl proton signals. The signal for 1,2-coupled polyisoprene was not observed. The $^1$H-NMR spectra were recorded in CDCl$_3$. The results of the experiments are compiled in Table 6.

TABLE 6

Summary of the polymerization results of isoprene

| Catalyst | Yield/ mg | Yield/ % | Polydispersity D | Chain length M$_w$/g/mol | Glass point/ °C | Coupling/ 1,4-cis: 1,4-trans: |
|---|---|---|---|---|---|---|
| Exp. 7 | 680 | 100 | 1.60 | 55582 | −55.4 | 70:14:16 |
| Exp. 8 | 260 | 38 | * | 58000* | −56.3 | 76:11:14 |

*Regarding Example 8, the GPC measurement revealed a multimodal distribution. The polydispersity can therefore not be determined; M$_w$ was graphically established from the elugram of the measurement.

The invention claimed is:

1. A homoleptic rare earth triaryl complex of formula 1

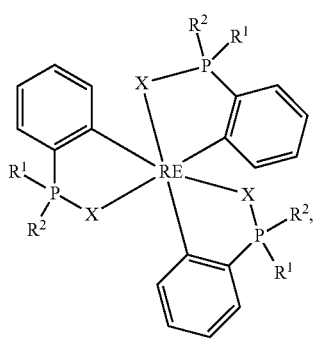

(1)

wherein
RE is Sc, Y, La, Ce, Pr, Nd, Pm, Sm, Eu, Gd, Tb, Dy, Ho, Er, Tm, Yb or Lu;
X is O or CRR'
R$^1$ and R$^2$ are phenyl;
R and R' are independently of each other, H, alkyl wherein n is from 1 to 10 carbon atoms, phenyl or trimethylsilyl.

2. A homoleptic rare earth triaryl complex according to claim 1, wherein when X is O, RE is Sc, Y, Lu or Yb.

3. A homoleptic rare earth triaryl complex according to claim 1, wherein when X is CH$_2$, RE is Se, Y, Lu, Sm, Gd or Dy.

4. A homoleptic rare earth triaryl complex according to claim 1 selected from the group consisting of:
[o-Sc(C$_6$H$_4$(C$_6$H$_5$)$_2$P═O)$_3$],
[o-Y(C$_6$H$_4$(C$_6$H$_5$)$_2$P═O)$_3$],
[o-Lu(C$_6$H$_4$(C$_6$H$_5$)$_2$P═O)$_3$],
[o-Yb(C$_6$H$_4$(C$_6$H$_5$)$_2$P═O)$_3$],
[o-Y(C$_6$H$_4$(C$_5$H$_5$)$_2$P═CH$_2$)$_3$],
[o-Sc(C$_6$H$_4$(C$_6$H$_5$)$_2$P═CH$_2$)$_3$],
[o-Lu(C$_5$H$_4$(C$_6$H$_5$)$_2$P═CH$_2$)$_3$],
[o-Dy(C$_6$H$_4$(C$_6$H$_5$)$_2$P═CH$_2$)$_3$],
[o-Gd(C$_6$H$_4$(C$_6$H$_5$)$_2$P═CH$_2$)$_3$], and
[o-Sm(C$_6$H$_4$(C$_6$H$_5$)$_2$P═CH$_2$)$_3$].

5. A method of preparing a homoleptic rare earth triaryl complex according to claim 1, wherein a compound of formula PhR$^1$R$^2$P═X, wherein X is O or CH$_2$ is reacted with a solvated rare earth metal halogenide or solvatized organo rare earth metal complex in the temperature range of −30° C. to 120° C.

6. The method according to claim 5, wherein the reaction is achieved by at least one of a salt elimination or hydrogen elimination.

7. The method according to claim 5, wherein the reaction is performed in situ as a one-pot reaction.

8. The method according to claim 5, wherein the reaction is performed in aromatics, cyclic ethers or in mixtures from these solvents.

9. The method according to claim 5, wherein the reaction is performed in a temperature range between 0° C. and 60° C.

10. The method according to claim 5, wherein the compound of formula PhR$^1$R$^2$P═X wherein X is O or CH$_2$ is reacted with a solvatized rare earth metal halogenide or solvatized organo rare earth metal complex at a molar ratio of 3:1.

11. The method according to claim 6, the reaction is a salt elimination and a lithium base is added in an equimolar amount to the compound of formula PhR$^1$R$^2$P═X, wherein X is O or CH$_2$.

12. A method of performing an organic reaction wherein the homoleptic rare earth triaryl complex of claim 1 is present as a reagent or catalyst for the organic reaction.

13. A method according to claim 12, wherein the homoleptic rare earth triaryl complex is present as a catalyst for an ring-opening polymerization in the production of polyester.

14. A method according to claim 12, wherein the homoleptic rare earth triaryl complex is present as a precatalyst for the polymerization of an olefin.

* * * * *